US009592167B2

United States Patent
Bogaerts et al.

(10) Patent No.: US 9,592,167 B2
(45) Date of Patent: Mar. 14, 2017

(54) FASTENING TAG FOR DISPOSABLE ABSORBENT ARTICLE

(75) Inventors: Bert Bogaerts, Boechout (BE); Anne Verhaert, Vorselaar (BE)

(73) Assignee: Avery Dennison Corporation, Glendale, CA (US)

( * ) Notice: Subject to any disclaimer, the term of this patent is extended or adjusted under 35 U.S.C. 154(b) by 135 days.

(21) Appl. No.: 14/115,904

(22) PCT Filed: May 7, 2012

(86) PCT No.: PCT/US2012/036754
§ 371 (c)(1),
(2), (4) Date: Nov. 6, 2013

(87) PCT Pub. No.: WO2012/154659
PCT Pub. Date: Nov. 15, 2012

(65) Prior Publication Data
US 2014/0088543 A1    Mar. 27, 2014

Related U.S. Application Data

(60) Provisional application No. 61/483,310, filed on May 6, 2011.

(51) Int. Cl.
*A61F 13/15* (2006.01)
*A61F 13/58* (2006.01)
*A61F 13/62* (2006.01)

(52) U.S. Cl.
CPC ............ *A61F 13/581* (2013.01); *A61F 13/58* (2013.01); *A61F 13/622* (2013.01); *A61F 13/625* (2013.01)

(58) Field of Classification Search
CPC ...... A61F 13/581; A61F 13/58; A61F 13/622; A61F 13/625
See application file for complete search history.

(56) References Cited

U.S. PATENT DOCUMENTS

| 4,058,125 A | 11/1977 | Ness |
| 4,067,337 A | 1/1978 | Ness |
| 4,726,971 A | 2/1988 | Pape et al. |
| 4,801,480 A | 1/1989 | Panza et al. |

(Continued)

FOREIGN PATENT DOCUMENTS

| DE | 102010026719 | 1/2011 |
| EP | 0321232 B1 | 5/1993 |

(Continued)

OTHER PUBLICATIONS dictionary.com, Sep. 16, 2015, dictionary.com, http://dictionary.reference.com/browse/region.*

(Continued)

*Primary Examiner* — Bradley Philips
(74) *Attorney, Agent, or Firm* — Avery Dennison Corporation

(57) ABSTRACT

A fastening tab that may be used with a disposable absorbent article such as a diaper, is disclosed. The fastening tab comprises a primary tape and a release tape. The primary tape may include a first and second mechanical fastener bearing region, an exposed adhesive region, and an intermediate region. The fastening tab provided may be directly attached to a nonwoven back sheet of a diaper chassis.

16 Claims, 5 Drawing Sheets

(56) References Cited

U.S. PATENT DOCUMENTS

| | | | |
|---|---|---|---|
| 5,108,384 A * | 4/1992 | Goulait | A61F 13/5512 604/389 |
| 5,549,591 A * | 8/1996 | Landvogt | A61F 13/62 604/389 |
| 5,897,546 A * | 4/1999 | Kido | A61F 13/5622 24/442 |
| 6,007,527 A * | 12/1999 | Kawaguchi | A61F 13/5512 156/315 |
| 6,096,420 A | 8/2000 | Wilhoit et al. | |
| 6,099,516 A | 8/2000 | Pozniak et al. | |
| 6,142,986 A * | 11/2000 | Lord | A61F 13/62 604/386 |
| 6,406,466 B1 | 6/2002 | Pozniak et al. | |
| 6,419,667 B1 * | 7/2002 | Avalon | A61F 13/581 24/442 |
| 6,719,744 B2 | 4/2004 | Kinnear et al. | |
| 7,438,709 B2 | 10/2008 | Karami et al. | |
| 2003/0032359 A1 * | 2/2003 | Kinnear | A61F 13/581 442/394 |
| 2004/0170794 A1 * | 9/2004 | Verhaert | A44B 18/0073 428/40.1 |
| 2005/0060849 A1 * | 3/2005 | Vanbenschoten | A44B 18/0049 24/451 |
| 2005/0261647 A1 | 11/2005 | Karami et al. | |
| 2005/0261650 A1 | 11/2005 | Damaghi et al. | |
| 2007/0039142 A1 * | 2/2007 | Petersen | A61F 13/581 24/448 |
| 2007/0134489 A1 * | 6/2007 | Neugebauer | A61F 13/15756 428/343 |
| 2007/0173781 A1 * | 7/2007 | Jackson | A61F 13/15756 604/391 |
| 2008/0097368 A1 * | 4/2008 | Molander | A61F 13/5622 604/391 |
| 2008/0195076 A1 * | 8/2008 | Coomans | A61F 13/581 604/391 |
| 2010/0004616 A1 * | 1/2010 | Nakamura | A61F 13/5622 604/389 |
| 2011/0004182 A1 * | 1/2011 | Hilston | A61F 13/15756 604/391 |
| 2013/0184671 A1 * | 7/2013 | Bogaerts | A61F 13/581 604/389 |
| 2014/0010984 A1 * | 1/2014 | Bogaerts | A61F 13/5622 428/41.8 |

FOREIGN PATENT DOCUMENTS

| | | |
|---|---|---|
| EP | 661959 | 7/1999 |
| EP | 0719534 B1 | 4/2000 |
| EP | 257752 | 1/2002 |
| EP | 919214 | 5/2003 |
| EP | 1725201 B1 | 12/2008 |
| WO | 9002540 | 3/1990 |
| WO | 2008033629 | 3/2008 |

OTHER PUBLICATIONS

International Search Report and Written Opinion dated Oct. 8, 2012 for International Patent Application No. PCT/US2012/036754, filed May 7, 2012.

* cited by examiner though the inventive subject matter is described herein in connection with a diaper, it is to be appreciated that aspects of the inventive subject matter find application to other like articles as well.

FASTENING TAG FOR DISPOSABLE ABSORBENT ARTICLE

CROSS-REFERENCE TO RELATED APPLICATION

The present application is a 371 of International Application No. PCT/US2012/036754, which was published in English on Nov. 15, 2012, which claims priority to U.S. Provisional Patent Application No. 61/483,310 filed May 6, 2011, which is incorporated herein by reference in its entirety.

BACKGROUND

The present inventive subject matter relates generally to the art of fastening tabs. Particular but not exclusive relevance is found in connection with disposable absorbent articles such as diapers, and accordingly the present specification makes specific reference thereto. It is to be appreciated however that aspects of the present inventive subject matter are also equally amenable to other like applications.

Disposable absorbent articles, such as baby diapers and/or incontinence diapers for adults, are generally known in the art. A typical diaper chassis is constructed of a liquid absorbent core enclosed between a liquid permeable topsheet (which is located adjacent a wearer when the diaper is worn) and a liquid impermeable backsheet (which forms an outer surface of the diaper when worn). The diaper chassis generally includes a rear portion intended to cover a wear's behind, a front portion intended to cover a wear's front and a crotch portion therebetween.

Commonly, diapers are provided with one or more fastening tabs. For example, two fastening tabs may be joined to the rear portion of the diaper chassis along opposing side ends or edges thereof. The fastening tabs may be joined directly to the chassis, or alternately, via intervening side panels. The fastening tabs allow each side of the rear portion of the diaper to be releasably attached to the front portion of the diaper thereby selectively forming a waistband around the wearer.

It is common for the front portion of the diaper to be provided with a landing strip arranged thereon to selectively receive the fastening tabs. For example, this landing strip may include a female portion of a mechanical fastening system. In particular, the landing strip often includes loop material designed to be engaged by corresponding hooks carried on the fastening tabs.

Recently, to reduce the cost and/or complexity of manufacturing diapers, it has become desirable to omit or eliminate the aforementioned landing strip. The use of a so called landing strip, also limits the area where the fastening tabs can be attached. Accordingly, it is further desirable to eliminate or omit the landing strip, so that the fastening tabs can be selectively attached to a larger area (e.g., essentially anywhere on the front portion of the diaper chassis to which they can reach). In any event, when the landing strip is eliminated or omitted, the fastening tabs are releasably attached directly to the backsheet forming the outer surface of the front portion of the diaper. As the backsheet is often constructed from a nonwoven material, it provides for some degree of engagement by the hooks typically carried on the fastening tabs. However, there can be difficulties in developing a fastening system that functions suitably (e.g., achieves a desirable degree of peel adhesion and/or shear strength) when the fastening tabs are attached directly to the diaper chassis backsheet. This problem is particularly evident in baby diapers which generally have smaller fastening tabs (due to their relatively smaller size) as compared to adult incontinence diapers which can generally accommodate larger fastening tabs. Indeed, as compared to baby diapers, adult incontinence diapers general have larger fastening tabs that can accommodate larger areas of mechanical fasteners (i.e., hooks). Moreover, adult diapers often have four tabs, e.g., two on each side, as compared to baby diapers which can often accommodate no more than a single tab on each side.

Accordingly, a new and/or improved fastening tab is disclosed which addresses the above-referenced problem(s) and/or others.

SUMMARY

This summary is provided to introduce concepts related to the present inventive subject matter. This summary is not intended to identify essential features of the claimed subject matter nor is it intended for use in determining or limiting the scope of the claimed subject matter.

In accordance with one embodiment, a fastening tab is provided for a disposable absorbent article, e.g., such as a baby diaper.

In accordance with a further embodiment, the fastening tab is designed to direct attachment to a nonwoven backsheet of the diaper chassis.

Numerous advantages and benefits of the inventive subject matter disclosed herein will become apparent to those of ordinary skill in the art upon reading and understanding the present specification.

BRIEF DESCRIPTION OF THE DRAWING(S)

The following detailed description makes reference to the figures in the accompanying drawings. However, the inventive subject matter disclosed herein may take form in various components and arrangements of components, and in various steps and arrangements of steps. The drawings are only for purposes of illustrating exemplary and/or preferred embodiments and are not to be construed as limiting. Further, it is to be appreciated that the drawings may not be to scale.

DETAILED DESCRIPTION

Figure 1:
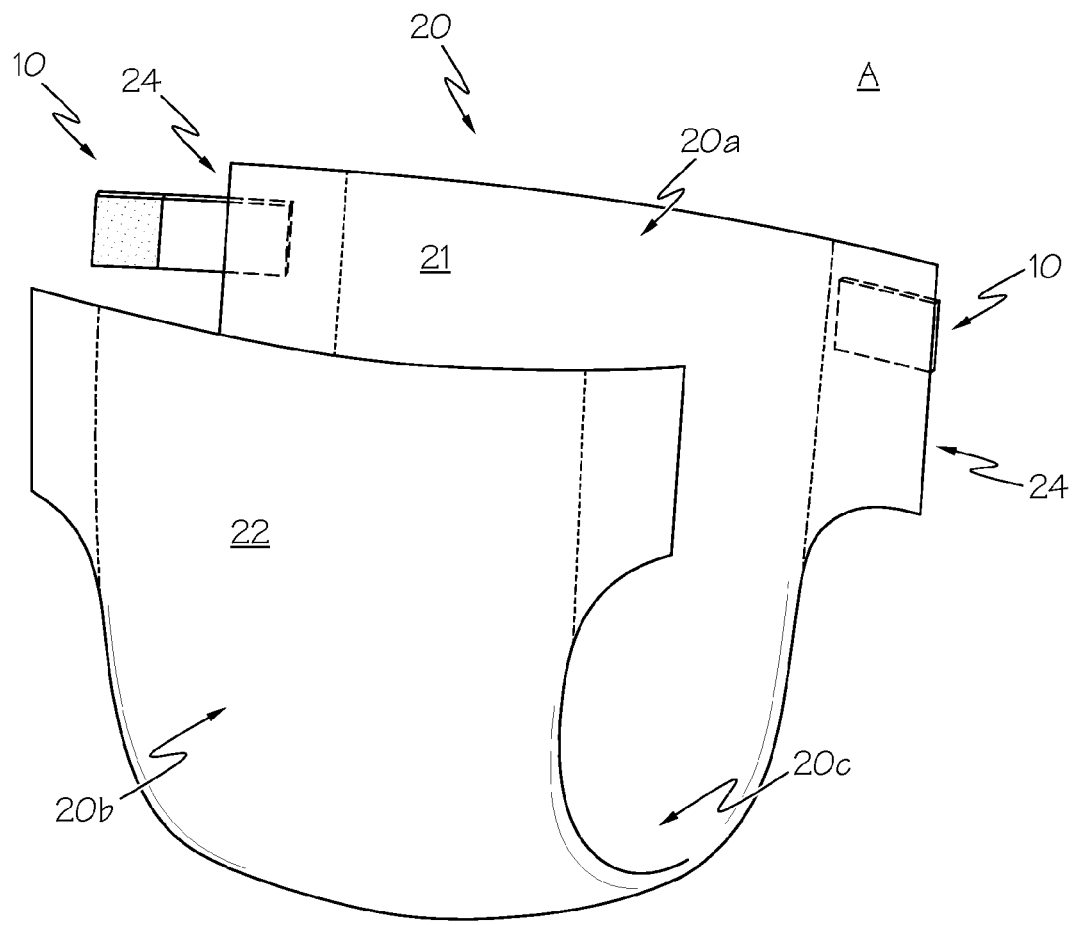
FIG. 1 is schematic illustration showing a disposable absorbent article including a pair of fastening tabs according to aspects of the present inventive subject matter.

With reference now to FIG. 1, there is shown a disposable absorbent article A (e.g., a baby diaper) including a pair of fastening tabs 10 joined to a diaper chassis 20. Notably, the left tab 10 is shown in an installed and deployed condition, while the right tab 10 is shown in an installed but un-deployed condition. In practice, the illustrated diaper chassis 20 is constructed of a liquid absorbent core (not shown) enclosed between a liquid permeable topsheet 21 (which generally forms an inner surface of the diaper located adjacent a wearer when the diaper is worn) and a liquid impermeable backsheet 22 (which generally forms an outer surface of the diaper when worn). The diaper chassis 20 generally includes a rear portion 20*a* intended to cover a wear's behind, a front portion 20*b* intended to cover a wear's front and a crotch portion 20*c* therebetween.

In the illustrated embodiment, the two fastening tabs 10 are joined to the rear portion 20*a* of the diaper chassis 20 along opposing side ends or edges 24 thereof. As shown, the fastening tabs 10 may be joined directly to the diaper chassis 20, or alternately, via intervening side panels (not shown) which may be elastic or inelastic. The fastening tabs 10 allow each side of the rear portion 20*a* of the diaper chassis 20 to be releasably attached to the front portion 20*b* of the diaper chassis 20 thereby selectively forming a waistband around a wearer.

Suitably, no landing strip or separate layer of loop material is provided for receiving the fastening tabs 10 on the front portion 20*b* of the diaper chassis 20. Rather, the fastening tabs 10 selectively engage with and/or releasably attach directly to the backsheet 22 forming the outer surface of the front portion 20*b* of the diaper chassis 20.

In practice, the backsheet 22 may be suitably formed from an appropriate nonwoven material. In one suitable embodiment, the backsheet 22 is formed from a spunbond nonwoven material having a weight in the range of approximately 10 gsm to approximately 25 gsm (grams per square meter), and more preferably in the range of approximately 12 gsm to approximately 20 gsm, and most preferably in the range of approximately 12 gsm to approximately 18 gsm. The nonwoven material suitably includes an entangled or otherwise arranged collection of fibers or filaments that may be thermally bonded or adhesively bonded to a polymer web or backing (e.g., a polyethylene backing). Of course, alternately, other known nonwoven materials may be similarly used and/or other known methods for manufacturing the nonwoven material may be employed.

Figure 2:
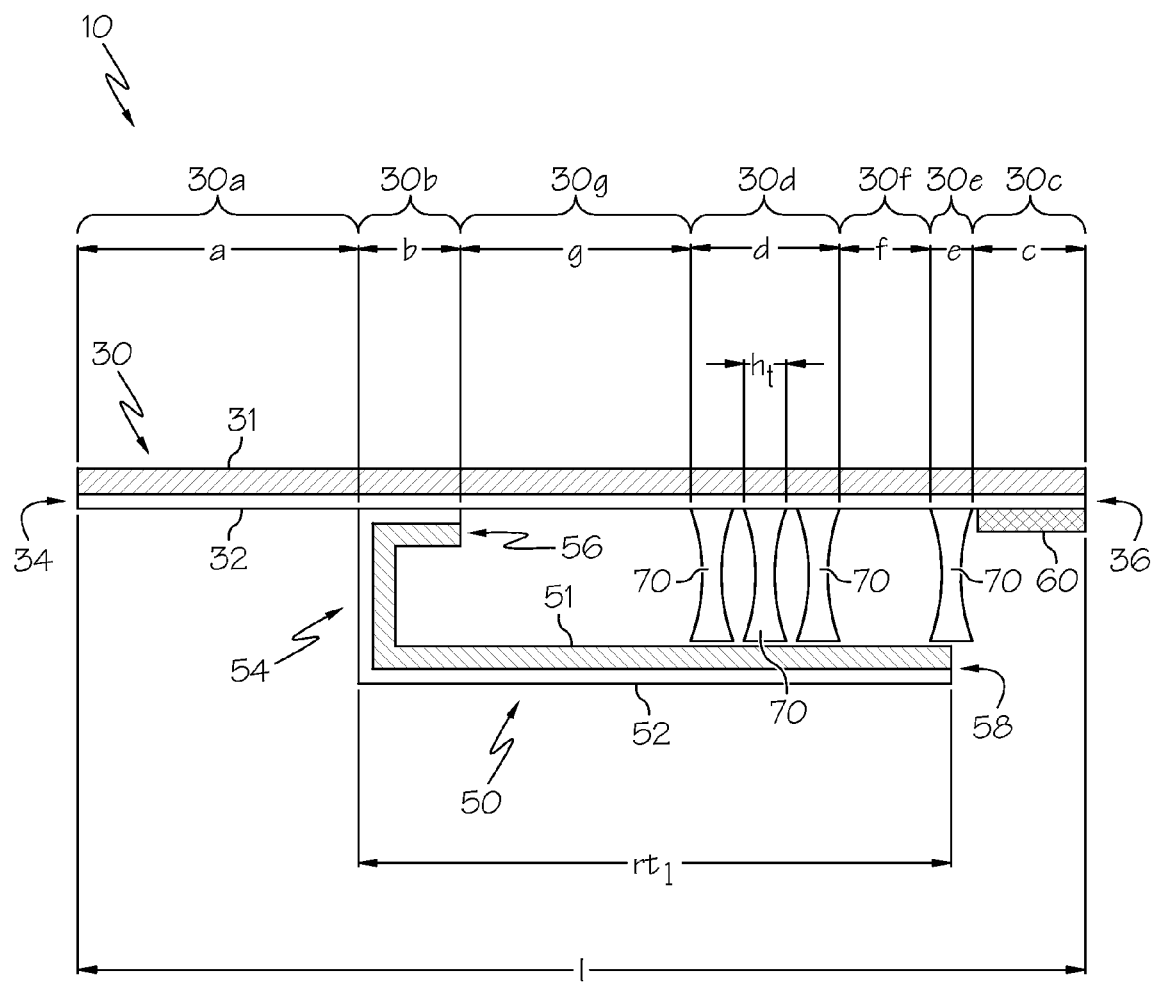
FIG. 2 is a schematic illustration showing one embodiment of an exemplary fastening tab according to aspects of the present inventive subject matter, the illustrated tab being in an uninstalled state.

With reference now to FIG. 2, there is shown an embodiment of an exemplary fastening tab 10 in a pre-installation or uninstalled condition, i.e., prior to attachment to the diaper chassis 20. Specifically, the fastening tab 10 is constructed of: a primary tape 30 including a substrate 31 having a layer of adhesive 32 arranged on one side thereof; and, a release tape 50 including a substrate 51 having a layer of adhesive 52 arranged on one side thereof. In the pre-installation condition, the primary tape 30 is unfolded and extends linearly to define the overall length "l" of the tab 10. For baby diaper applications, the length l is suitably in the range of approximately 45 mm (millimeters) to approximately 70 mm. In one exemplary embodiment, the length l is approximately 62 mm.

The primary tape 30 includes a manufacturer's end 34 that is intended to be joined by the manufacturer, e.g., to a side end or edge 24 of the rear portion 20*a* of the diaper chassis 20, and an opposing free or user's end 36 that a user may selectively employ to releasably attached the fastening tab 10, e.g., to the front portion 20*b* of the diaper chassis 20. Suitably, the release tape 50 includes a fold or hinge 54 formed in the tape 50 between a first end 56 of the release tape 50 and an opposing second end 58 of the release tape 50. As shown, the fold or hinge 54 is arranged nearer the first end 56 of the release tape 50 as compared to the second end 58 thereof. The portion of the release tape 50 residing between first end 56 thereof and the fold or hinge 54 is in turn joined to the primary tape 30 via the adhesive layers 32 and/or 52 of the respective tapes 30 and 50.

As shown, the primary tape 30 has a plurality of functional areas or distinct zones, including:

- a manufacturer's end portion 30*a*, which is the portion of the tape 30 spanning from the manufacturer's end 34 of the tape 30 to where the release tape 50 attaches to the primary tape 30;
- a release tape attachment area 30*b*, which is the portion of the tape 30 to which the release tape 50 is joined at its first end 56;
- a finger-lift area 30*c*, which is the portion of the tape 30 immediately adjacent the free or user end 36 of the tape 30;
- first and second mechanical fastener bearing regions 30*d* and 30*e*, respectively, which correspond to those portions of the tape 30 carrying mechanical fasteners (e.g., such as hooks or the like which are commonly used in hook and loop type fastening systems);
- an exposed adhesive region 30*f*, which is that portion of the tape 30 spanning a gap between the mechanical fastener bearing regions 30*d* and 30*e*; and
- an intermediate region 30*g*, which is that portion of the tape 30 between the first mechanical fastener bearing region 30*d* and the release tape attachment area 30*b*. Collectively, the portions 30*c* through 30*g* are referred to herein as the deployment zone or portion of the tape 30. Suitably, as shown, the release tape 50 overlaps and/or covers the primary tape 30 from the release tape attachment area 30*b* to at least a portion of the second mechanical fastener bearing region 30*e*. In a baby diaper application (e.g., with an overall tab length l of approximately 62 mm), suitably, the length "$rt_i$" of the release tape 50 from the fold or hinge 54 to the second end 58 of the tape 50 is approximately 35 mm, and the release tape attachment area 30*b* has a length "b" of approximately 5.5 mm.

The finger-lift area 30*c* at the user end 36 of the tape 30 provides a region substantially free of exposed adhesive that a user may readily grasp (e.g., between his thumb and forefinger) to selectively deploy the fastening tab 10 and/or to selectively attach and/or detach the deployment zone of the tape 30, e.g., to and/or from the front portion 20*b* of the diaper chassis 20. As shown in FIG. 2, a non-adhesive film or layer or other like cover 60 is joined to the primary tape 30 by the adhesive 32 in the finger-lift area 30*c*. The cover 60 (as the name suggests) overlaps and/or otherwise covers all or most of the finger-lift area 30*c* to thereby substantially limit or eliminate any exposure of the underlying adhesive layer 32. Alternately, the finger-lift area 30*c* may simply have the adhesive 32 omitted therefrom, e.g., by pattern coating the adhesive 32 on the substrate 31 so that no adhesive 32 is deposited in the finger-lift area 30*c*. In yet another embodiment, the finger-lift area 30*c* may be formed by folding over the free end 36 of the tape 30 onto itself so that the adhesive layer 32 is sandwiched between the substrate 31. In yet another embodiment, an adhesive deadener may be applied to the adhesive 32 in the finger-lift area 30*c* thereby substantially reducing or eliminating the adhesive properties of the so treated adhesive 32. Suitably, in a baby diaper application (e.g., with a tab length l of approximately 62 mm), the length "c" of the finger-lift area 30*c* is in the range of approximately 4 mm to approximately 10 mm. In one suitable example, the finger-lift area 60 is approximately 7 mm.

The first and second mechanical fastener bearing regions 30d and 30e each carry mechanical fasteners joined thereto by the underlying adhesive 32. Suitable mechanical fasteners include hook material or the like which is commonly used in hook and loop type fastening systems. The hook material may include a base or substrate (e.g., secured to the tape 30 by the adhesive layer 32) with a plurality of upstanding members projecting outward therefrom, such members having hook-shaped or mushroom-shaped or otherwise shaped heads designed for mechanical engagement with a counterpart loop or suitable nonwoven material. Alternately, the hook material or other mechanical fasteners may be bonded to the primary tape 30 and/or the substrate 31 using any suitable method or technique known in the art, including, but not limited to, adhesive bonding (for example, pressure sensitive or hot melt), hot bonding or ultrasonic bonding.

As shown, the second mechanical fastener bearing region 30e carries a single lane of hook material 70 immediately adjacent the finger-lift area 30c. Optionally, a small gap (e.g., approximately 0.5 mm) of exposed adhesive 32 may exist between the lane of hook material 70 and the cover 60 overlapping the finger-lift area 30c. The first mechanical fastener bearing region 30d suitably carries multiple lanes of hook material 70 with small gaps (e.g., approximately 0 mm to approximately 5 mm) of exposed adhesive 32 therebetween. As shown, there are three lanes of hook material 70 carried in the first mechanical fastener bearing region 30d, however, in practice, more or fewer lanes of hook material 70 may be carried in the region 30d. Alternately, a single uninterrupted span of hook material may be carried in the region 30d. Suitably, each lane of hook material 70 has a length "$h_l$" in the range of approximately 2 mm to approximately 25 mm, and preferably that range is approximately 2 mm to approximately 13 mm, and more preferably that range is approximately 2 mm to approximately 5 mm.

Between the first and second mechanical fastener bearing regions 30d and 30e, there is a gap comprising a portion 30f of the tape 30 in which the adhesive layer 32 is exposed, i.e., the adhesive 32 is not covered by mechanical fasteners or a cover or the like. Suitably, in a baby diaper application (e.g., with a tab length l of approximately 62 mm), the length "f" of the exposed adhesive region 30f is approximately 5 mm. While the schematic illustrations show a space between the adhesive region 30f of the primary tape 30 and a corresponding overlapping region of the release tape 50, it is to be appreciated that in practice these two regions are in contact with one another and releasably adhered together via the adhesive 32. This releasable bond helps guard against unwanted flagging. In other words, the releasable bond formed at the adhesive region 30f between the tape 30 and the tape 50 functions to hold the respective tapes together and/or adjacent one another, e.g., during diaper manufacture, tab installation, storage, etc.—that is, until such time as selective deployment of the deployment zone is desired and the respective releasable bond is intentionally broken.

In applications for baby diapers (e.g., where the overall length of the tab 10 is approximately 62 mm), suitably, the first mechanical fastener bearing region 30d has a length "d" in the range of approximately 0 mm to approximately 25 mm (preferably, d is in the range of approximately 5 mm to approximately 20 mm, and more preferably d is in the range of approximately 10 mm to approximately 15 mm) and the second mechanical fastener bearing region 30e has a length "e" in the range of approximately 2 mm to approximately 25 mm (preferably, e is in the range of approximately 2 mm to approximately 15 mm, and more preferably e is in the range of approximately 2 mm to approximately 10 mm). Moreover, in such applications, suitably, the first and second regions 30d and 30e along with the gap 30f therebetween have a total length in the range of approximately 0 mm to approximately 30 mm, preferably in the range of approximately 10 mm to approximately 30 mm, and more preferably in the range of approximately 20 mm to approximately 30 mm.

The intermediate region 30g is that portion of the tape 30 which extends between the first mechanical fastener bearing region 30d and the release tape attachment area 30b. As shown in FIG. 2, the intermediate region 30g may also have exposed adhesive 32, i.e., the adhesive 32 in the intermediate region 30g may not be covered by mechanical fasteners or a cover or the like. Suitably, in a baby diaper application, the length "g" of the intermediate region 30g is in a range of between approximately 0 mm and 15 mm (preferably, g is in the range of approximately 5 mm to approximately 10 mm). Again, while the schematic illustration shows a space between the region 30g of the primary tape 30 and a corresponding overlapping region of the release tape 50, it is to be appreciated that in practice these two regions are in contact with one another and releasably adhered together via the adhesive 32. This releasable bond again helps to guard against unwanted flagging. In other words, the releasable bond formed at the region 30g between the tape 30 and the tape 50 functions to hold the respective tapes together and/or adjacent one another, e.g., during diaper manufacture, tab installation, storage, etc.—that is, until such time as selective deployment of the deployment zone is desired and the respective releasable bond is intentionally broken.

Figure 3:
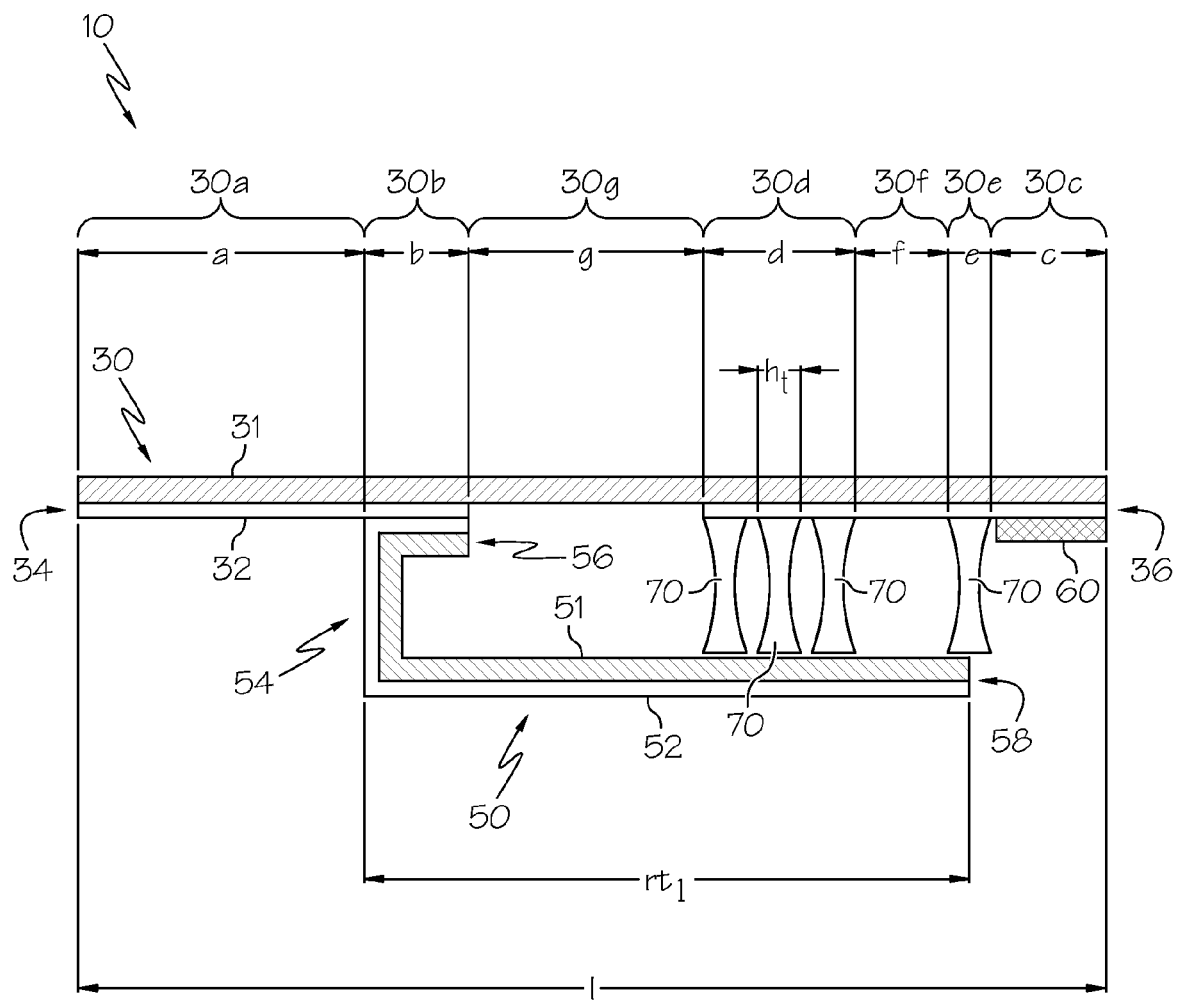
FIG. 3 is a schematic illustration showing another embodiment of an exemplary fastening tab according to aspects of the present inventive subject matter, the illustrated tab being in an uninstalled state.

FIG. 3 shows another exemplary embodiment of the fastening tab 10. This embodiment is similar to the embodiment shown in FIG. 2. However, the adhesive 32 has been omitted or eliminated from the intermediate region 30g of primary tape 30. Suitably, omission of the adhesive 32 from the region 30g is achieve by pattern coating the substrate 31 with adhesive 32 such that no adhesive 32 is deposited in the region 30g. Alternately, if one wishes to avoid the burden of pattern coating, a functionally similar result can be achieved by providing a cover (e.g., similar to the cover 60) that overlaps and/or otherwise substantially covers the adhesive layer 32 otherwise provided in the region 30g. In yet another embodiment, a functionally similar result can be achieved by treating the adhesive layer 32 in the intermediate region 30g with an adhesive deadener to substantially reduce or eliminate the adhesive properties of the so treated adhesive 32.

Figure 4:
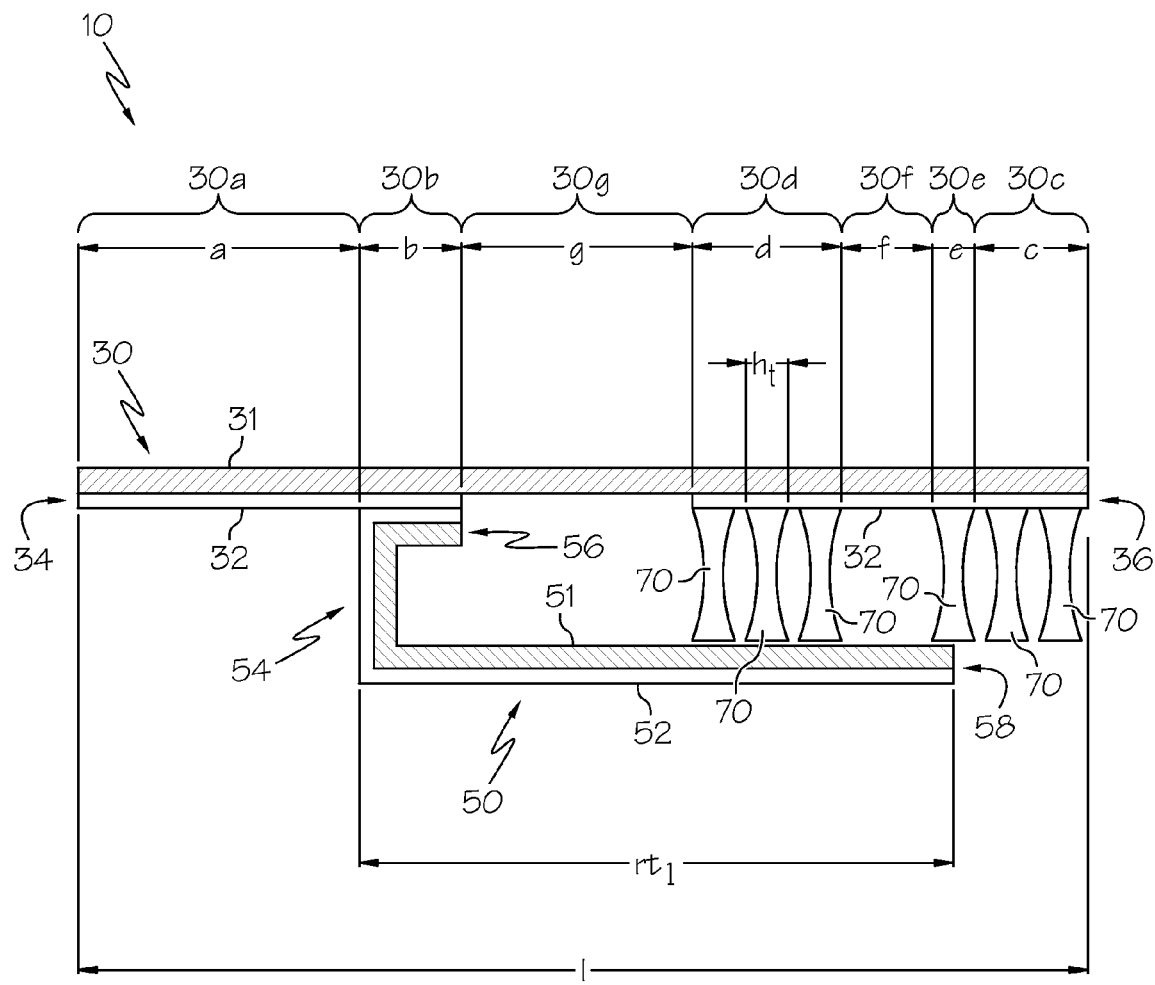
FIG. 4 is a schematic illustration showing yet another embodiment of an exemplary fastening tab according to aspects of the present inventive subject matter, the illustrated tab being in an uninstalled state.

FIG. 4 shows yet another exemplary embodiment of the fastening tab 10. This embodiment is similar to the embodiment shown in FIG. 3. However, the cover 60 has been replaced with mechanical fasteners. In particular, as shown in FIG. 4, a number of lanes of hook material 70 are carried in the finger-lift area 30c, attached thereto by the underlying adhesive 32. Alternately, more or less lanes of hook material 70 may be used or a single uninterrupted span of hook material may be used in the finger-lift area 30c. In yet another embodiment, a single uninterrupted span of hook material may be used for both the finger-lift area 30c and the second mechanical fastener bearing region 30e of the tape 30. Often, the finger-lift area 30c or end 36 of the tape 30 is made to remain free of adhesive and/or mechanical fasteners (e.g., as shown in FIG. 2) so as to not attach to the front portion 20b of the diaper chassis 20 when the deployment zone of the tape 30 is applied thereto. Accordingly, even when the deployment zone of the tape 30 is applied as indicated, there remains a free end 36 on the tape 30 (unattached to the front portion 20b of the diaper chassis 20) that a user can easily grasp at a subsequent time, e.g., to remove and/or reapply the deployment zone of the tape 30 as desired. In the current application, however, where the deployment zone of the tape 30 is directly applied to the nonwoven material comprising the backsheet 22 forming the front portion 20b of the diaper chassis 20, it may be desirable to fasten down the finger-lift area 30c and/or end 36 of the tape 30 somewhat with mechanical fasteners or hook material in order to guard against an unwanted/accidental release of the tape 30, e.g., as might occur if the finger-lift area 30c and/or end 36 of the tape 30 were totally free and hence more subject to rubbing and/or pulling or otherwise getting caught on a wearer's clothing or the like as they move around. Since in the current application the deployment zone of the tape 30 will be fastened directly to the nonwoven material making up the backsheet 22 of the front portion 20b of the diaper chassis 20 itself, as opposed to a loop material or specialized landing strip with a relatively greater grip, the fastening strength provided by the hooks or mechanical fasteners in the finger-lift area 30c and/or at the end 36 of the tape 30 will be somewhat limited. Accordingly, having hook material and/or other like mechanical fasteners in the finger-lift area 30c and/or at the end 36 of the tape 30 (e.g., as shown in FIG. 4) will not present an unacceptable degree of peel and/or lift resistance such that a user would not still be able to readily free and/or grasp the finger-lift area 30c and/or end 36 of the tape 30 in a deliberate attempt to do so. However, with hook material and/or other like mechanical fasteners arranged in the finger-lift area 30c and/or at the end 36 of the tape 30, some degree of fastening strength will be provided to help hold the finger-lift area 30c and/or end 36 of the tape 30 against the nonwoven outer surface of the backsheet 22 forming the front portion 20b of the diaper chassis 20, and accordingly, this will guard against an unwanted and/or unintentional release of the deployment zone of the tape 30 therefrom.

Figure 5:
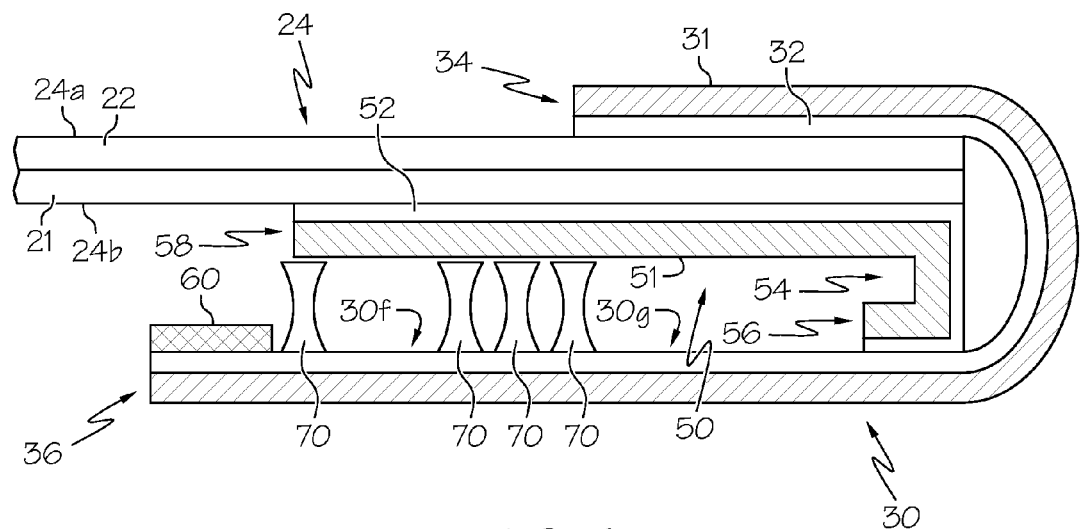
FIG. 5 is a schematic illustration showing the fastening tab of FIG. 2 in an installed but un-deployed stated.

With reference now to FIG. 5, it is shown how the fastening tab 10 is installed, i.e., joined or otherwise secured to the diaper chassis 20. In particular, FIG. 5 illustrates the embodiment of the tab 10 shown in FIG. 2 being installed along one side end or edge 24 of the rear portion 20a of the diaper chassis 20. However, it is to be appreciated that other embodiments of the tab 10, may also be installed in a similar fashion. Regardless, as shown, the side end or edge 24 of the diaper chassis 20 includes a first surface 24a (e.g., corresponding to the outer surface of the diaper chassis 20) provided by the topsheet 21, and a second opposing surface 24b (e.g., corresponding to the inner surface of the diaper chassis 20) provided by the backsheet 22. Of course, in practice, where the tab 10 is joined or otherwise connected to an optional side panel, either an extension of the topsheet 21 alone or an extension of the backsheet 22 alone or another separate side panel piece may provide the opposing first and second attachment surfaces 24a and 24b for the tab 10.

In any event, suitably, the adhesive 32 residing in the manufacturer's end portion 30a of the primary tape 30 is contacted to the first tab attachment and/or outer surface 24a of the side end or edge 24 of the rear portion 20a of the diaper chassis 20 to thereby secure and/or join the primary tape 30 thereto. Suitably, for a baby diaper application (e.g., wherein the overall length l of the tab 10 is approximately 62 mm), the length "a" of the of the manufacturer's end portion 30a of the primary tape 30 is approximately 10 mm to approximately 25 mm (preferably, a in the range of approximately 15 mm to approximately 20 mm). The tab 10 is then folded over the end or edge 24 thereby bringing the adhesive layer 52 between the fold or hinge 54 and the second end 58 of the release tape 50 into contact with the second tab attachment and/or inner surface 24b of the side end or edge 24 of the rear portion 20a of the diaper chassis 20 to thereby secure and/or join the release tape 50 thereto. In this manner, a so called Y-bond is formed securing the tab 10 to the diaper chassis 20 (or side panel as the case may be) with side end or edge 24 of the rear portion 20a adhesively sandwiched between the release tape 50 and the manufacturer's end portion 30a of the primary tape 30.

Figure 6:
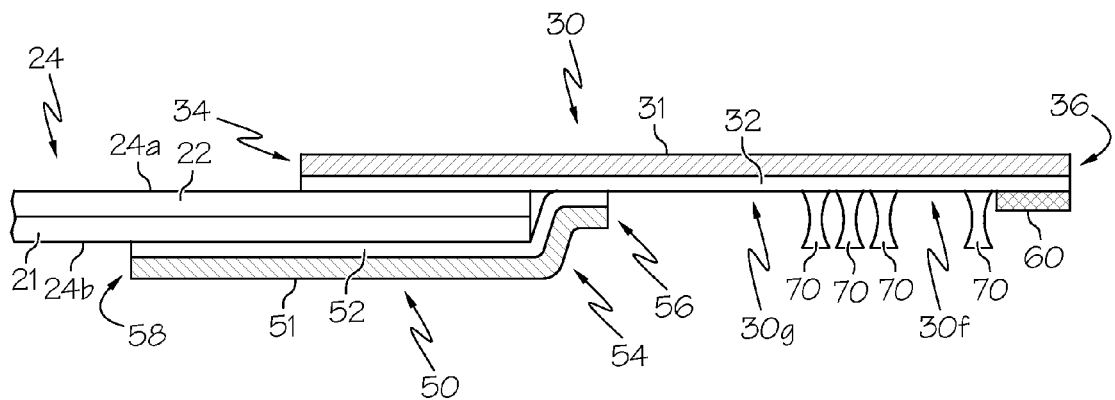
FIG. 6 is a schematic illustration showing the fastening tab of FIG. 2 in an installed, deployed stated.

To use the fastening tab 10, the deployment zone of the primary tape 30 is first exposed. That is to say, the primary tape 30 is unfolded and extended laterally (e.g., as shown in FIG. 6) from the un-deployed state (e.g., as shown in FIG. 5). In particular, the finger-lift area 30c may be grasped by a user and pulled so that the releasable bond between the adhesive region 30f and the release tape 50 and any releasable bond between the intermediate region 30g and the release tape 50 are broken as the deployment zone of the primary tape 30 is pivoted away from the release tape 50. Accordingly, the fold or hinge 54 of the release tape 50 is opened so that the portion of the release tape 50 between the first end 56 thereof and the fold or hinge 54 remains joined to the primary tape 30 and the portion of the release tape 50 between the second end 58 thereof and the fold or hinge 54 remains joined to the side end or edge 24 of the rear portion 22a of the diaper chassis 20 (or alternately to the diaper side panel as the case may be).

At this point, the exposed deployment zone of the primary tape 30 is selectively pressed to and/or otherwise contacted with outer surface of the nonwoven backsheet 22 forming the front portion 20b of the diaper chassis 20, thereby releasably attaching the fastening tab 10 thereto. Notably, the mechanical fasteners carried in respective areas of the deployment zone of the primary tape 30 suitably engage with the fibers of the nonwoven backsheet 22 while exposed adhesive in the deployment zone of the primary tape 30 releasably adhere to the nonwoven backsheet 22. Significantly, the disclosed combinations of mechanical fastener bearing regions and exposed adhesive areas in the deployment zone of the primary tape 30 provide a functionally desirable fastener (i.e., exhibiting suitable peel adhesion and shear strength) for direct attachment to the nonwoven backsheet 22 of the diaper chassis 20, particularly in applications for baby diapers where the relatively small diaper size (e.g., as compared to adult incontinence diapers) can limit in practice the size of the fastening tab 10.

Notably, the combination of alternating regions of mechanical fasteners and exposed adhesive (e.g., mechanical fastener region 30e, follow by adhesive region 30f, followed by mechanical fastener region 30d, followed by adhesive region 30g) achieves a desirable tab performance—i.e., good closure and/or releasable attachment to a nonwoven backsheet marked by functional levels of peel adhesion and shear strength. Additionally, separation of the adhesive regions on the primary tape 30 by intervening mechanical fasteners protects against excessive tear-out of the nonwoven backsheet fibers by the adhesive regions when the tape 30 is removed therefrom. As can be appreciated, this protects the nonwoven backsheet from excessive wear and tear and protects the adhesive areas of the tape 30 from becoming contaminated with torn-out fibers, thereby guarding against degradation of re-closure performance.

The herein described fastening tabs 10 beneficially achieve a functionally operative closure system for a wide range of different types of nonwoven backsheets commonly used in the production of baby diapers. However, it is to be appreciated that the tab parameters can be selected to achieve the desire performance depending on the particular nonwoven backsheet for which it is intended. For example, nonwoven backsheets in which the fiber mass is adhesively bonded together and/or to an underlying support film tend to have more tightly packed and/or bound fibers due to the production process for such nonwovens as compared to thermo-bonded nonwovens. Accordingly, for thermo-bonded nonwovens which tend to have a greater availability of and/or looser fibers for engagement with mechanical fasteners, the ratio of mechanical fastener bearing area to exposed adhesive area on the tape 30 can optionally be increased, while conversely, for adhesive-bonded nonwovens which tend to have less available and/or more tightly bound fibers for engagement with mechanical fasteners, the ratio of exposed adhesive area to mechanical fastener bearing area on the tape 30 can optionally be increased. Notably, increasing the exposed adhesive areas on the tape 30 in the latter case can be safely done without as much concern for the aforementioned fiber tear-out problem insomuch as the nonwoven fibers are generally more tight held by the nonwoven in this case, e.g., as compared to thermo-bonded nonwovens.

Suitably, the substrates 31 and 51 can be made of cloth, kraft paper, cellophane film, nonwoven webs, polymeric films (e.g., polypropylene, polyethylene terephthalate, and polyethylene) or other suitable materials or laminates. The non-adhesive sides of the substrates can include release coatings (e.g., a silicone coating, a carbamate coating, etc.) if such is desirable, e.g., to prevent blocking issues during assembly, storing, and/or dispensing the fastener tabs 10 for installation on the diaper chassis 20. If the substrate 31 is to be elastic, substrate selection could include extruded or coextruded elastic films that are monolayers or that include suitable skins, backings, or release linings.

The adhesive layers 32 and 52 can be any conventional adhesive, including pressure sensitive adhesives and non-pressure sensitive adhesives. Suitable pressure sensitive adhesives include acrylic resin and natural or synthetic based rubber adhesives. Optionally, the fastener tab 10 can be advantageously constructed of substrates 31 and 51 with continuous adhesive layers 32 and 52 arranged on one side thereof. That being said, patterned-coated adhesive layers are certainly possible and contemplated, and may even be preferred in certain embodiments.

Suitably, the hook base or substrate can be made of any material that is compatible with the hook-production process and accommodates its hook-carrying function. The hooks can be made of a plastic, metal or other material and formed by, for example, molding or stamping. If the hook substrate and the hooks are separately formed, the hook substrate can be made of, for example, cloth, kraft paper, cellophane film, nonwoven webs, and/or polymeric films. Attachment of the hooks to a separately-formed base or substrate can be accomplished, for example, by adhesive bonding or hook-embedment. Alternatively, the hook substrate or base and the hooks can be integrally formed (e.g., stamping, molding, etc.) whereby they are made of the same material. The hooks can have a variety of "hooking" shapes such as, for example, a J-shape geometry, a mushroom-shape geometry, an arrow-shape geometry, a barbed geometry, and/or a bulbous geometry. However any conventional hooking shapes can be used in accordance with this invention. Although not specifically shown in the drawings, an adhesive layer can be provided on the side of the hook substrate or base opposite its hook-carrying side.

The cover 60 for the finger-lift area 30c (and/or optionally for the intermediate region 30g) can be made of any suitable material. For example, they can be made of cloth, kraft paper, cellophane film, nonwoven webs, polymeric films (e.g., polypropylene, polyvinyl chloride, polyethylene terephthalate, and polyethylene) and/or combinations thereof. In most instances, the adhesive 32 will be sufficient for bonding purposes as they are usually not subjected to any forces that would encourage detachment.

Although the fastener tab, the tape segments, the tapes, the laminates, and corresponding systems and methods have been shown and described with respect to a certain embodiment or embodiments, it is obvious that equivalent alterations and modifications will occur to others skilled in the art upon the reading and understanding of this specification and the annexed drawings. In regard to the various functions performed by the above described elements (e.g., components, assemblies, systems, devices, compositions, etc.), the terms (including a reference to a "means") used to describe such elements are intended to correspond, unless otherwise indicated, to any element that performs the specified function of the described element (i.e., that is functionally equivalent), even though not structurally equivalent to the disclosed structure that performs the function. In addition, while a particular feature of the invention may have been described above with respect to only one or more of several illustrated embodiments, such a feature may be combined with one or more other features of the other embodiments, as may be desired and advantageous for any given or particular application.

In short, it is to be appreciated that the present specification has been set forth with reference to exemplary embodiments. Obviously, modifications and alterations will occur to others upon reading and understanding the present specification. It is intended that the invention be construed as including all such modifications and alterations insofar as they come within the scope of the appended claims or the equivalents thereof.

What is claimed is:

1. A fastening tab for a diaper, said tab comprising:
    a primary tape including a primary tape substrate having
        a layer of primary tape adhesive arranged on a first side of the primary tape substrate; and,
    a release tape joined to the primary tape, said release tape including a release tape substrate having a layer of release tape adhesive arranged on a first side of the release tape substrate;
    wherein said primary tape includes:
        a release tape attachment area, which is a portion of the primary tape to which the release tape is joined at its first end;
        a first mechanical fastener bearing region carrying mechanical fasteners;
        a second mechanical fastener bearing region carrying mechanical fasteners;
        an exposed adhesive region which spans a gap between the first mechanical fastener bearing region and the second mechanical fastener bearing region; and
        an intermediate region which is a portion of the primary tape between the first mechanical fastener bearing region and the release tape attachment area and which has exposed adhesive therein,
    wherein the release tape attachment area is disposed between the first mechanical fastener bearing region and a manufacturer's end so that the release tape overlaps and/or covers the primary tape from the release tape attachment area to at least a portion of the second mechanical fastener bearing region, wherein a finger-lift region that bears mechanical fasteners thereon is disposed between the second mechanical fastener bearing region and a user's end, and wherein the release tape does not overlap or cover the finger lift region.

2. The fastening tab of claim 1, wherein the primary tape further includes a manufacturer's end portion and a user's end portion.

3. The fastening tab of claim 1, wherein the release tape attachment area has a length of approximately 5.5 mm.

4. The fastening tab of claim 1, wherein the primary tape, when unfolded, extends linearly and defines an overall length in the range of approximately 45 mm to approximately 20 mm.

5. The fastening tab of claim 1, wherein the substrates are made of cloth, kraft paper, cellophane film, nonwoven webs, polymeric films, or other suitable materials or laminates.

6. The fastening tab of claim 1, wherein the primary tape substrate is elastic and includes extruded or coextruded elastic films that are monolayers or that include suitable skins, basking, or release lining.

7. The fastening tab of claim 1, wherein the release tape includes a fold or hinge formed in the release tape between a first end of the release tape and an opposing second end of the release tape.

8. The fastening tab of claim 1, wherein the mechanical fasteners are hook and loop type fastening systems.

9. The fastening tab of claim 1, wherein the mechanical fasteners are bonded to the primary tape and/or substrate by adhesive bonding, hot bonding, or ultrasonic bonding.

10. The fastening tab of claim 1, wherein the finger-lift area is free of adhesive.

11. A disposable absorbent article including at least one fastening tab as essentially shown and described in any of the preceding claims.

12. The fastening tab of claim 1, wherein the mechanical fasteners of the finger lift comprise hook material.

13. The fastening tab of claim 1, wherein the second mechanical fastener bearing region carries a single lane of hook material.

14. The fastening tab of claim 1, wherein the first mechanical fastener bearing region carries multiple lanes of hook material.

15. A disposable absorbent article comprising:

a pair of fastening tabs wherein each fastening tab comprises a primary tape and a release tape;

wherein said primary tape includes:

a release tape attachment area, which is a portion of the primary tape to which the release tape is joined at its first end;

a first mechanical fastener bearing region carrying mechanical fasteners;

a second mechanical fastener bearing region carrying mechanical fasteners;

an exposed adhesive region which spans a gap between the first mechanical fastener bearing region and the second mechanical fastener bearing region; and an intermediate region which is a portion of the primary tape between the first mechanical fastener bearing region and the release tape attachment area and which has exposed adhesive therein, wherein the release tape attachment area is disposed between the first mechanical fastener bearing region and a manufacturer's end so that the release tape overlaps and/or covers the primary tape from the release tape attachment area to at least a portion of the second mechanical fastener bearing region, wherein a finger-lift region that bears mechanical fasteners thereon is disposed between the second mechanical fastener bearing region and a user's end, and wherein the release tape does not overlap or cover the finger lift region a diaper chassis having a rear and front portion wherein the diaper chassis is constructed of a core and a backsheet; and wherein the fastening tabs are joined to the rear portion of the diaper chassis.

16. The fastening tab of claim 13, wherein the first mechanical fastener bearing region carries multiple lanes of hook material.

\* \* \* \* \*